(12) United States Patent
Puri et al.

(10) Patent No.: US 6,660,861 B1
(45) Date of Patent: Dec. 9, 2003

(54) PROCESS FOR PREPARING TOPOTECAN FROM 10-HYDROXY-4-(S) CAMPTOTHECIN

(75) Inventors: Satish Chander Puri, Jammu (IN); Geeta Handa, Jammu (IN); Kanaya Lal Dhar, Jammu (IN); Om Parkash Suri, Jammu (IN); Ghulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/401,119

(22) Filed: Mar. 27, 2003

(51) Int. Cl.$^7$ .............................................. C07D 491/14
(52) U.S. Cl. ........................................................ 546/48
(58) Field of Search ............................................ 546/48

(56) References Cited

FOREIGN PATENT DOCUMENTS

WO    WO 94/05672    *    3/1994

* cited by examiner

Primary Examiner—Patricia L. Morris
(74) Attorney, Agent, or Firm—Ladas & Parry

(57) ABSTRACT

The present invention relates to the use of dihalomethanes as reagents for the preparation of Topotecan{4-(S)-10 (dimethylamino)-methyl-4-ethyl 4,9 dihydroxyl-H-pyrano [3'4':6,7]indolizino-[1,2-b]quinoline-3,14(4H,12H)dione} from 10-hydroxycamptothecin. The invention discloses the rationale use of dichloromethane under solid-liquid phase transfer catalysis, which can behave both as solvent and a reactant when it serves as a source for C-1 unit for aminoalkylation of 10-hydroxy-4-(S)camptothecin.

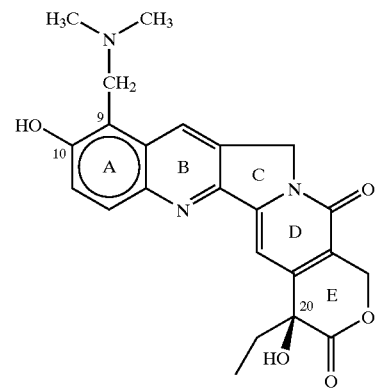

Topotecan(TPT)

10 Claims, No Drawings

PROCESS FOR PREPARING TOPOTECAN FROM 10-HYDROXY-4-(S) CAMPTOTHECIN

FIELD OF THE INVENTION

The present invention relates to the use of dihalomethanes as reagents for the preparation of Topotecan{4-(S)-10 (dimethylamino)-methyl-4-ethyl 4,9 dihydroxyl-H-pyrano [3'4':6,7]indolizino-[1,2-b]quinoline-3,14(4H,12H)dione} of formula I from hydroxycamptothecin. The invention discloses the rationale use of dichloromethane under solid-liquid phase transfer catalysis, which can behave both as solvent and a reactant when it serves as a source for C-1 unit for amino-alkylation of 10-hydroxy-4-(S)camptothecin.

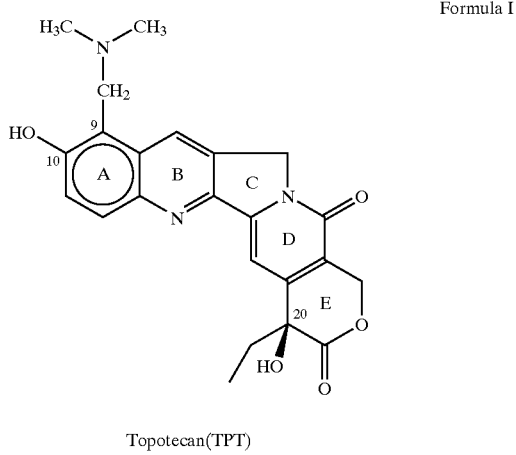

Topotecan(TPT)

BACKGROUND OF THE INVENTION

Topotecan (TPT)[9-(dimethylamino)-methyl]-10-hydroxy-(4S)-camptothecin) which is of the chemical structure of Formula I, is under clinical trials and its chemotherapeutic efficacy appears to be very promising. (Slichenmyer, W. J., Rowinsky, E. K., Donehower, R. C., J. Natl. Cancer Inst., 85:271 1993) Topotecan is one of he new class agents those targets topoisomerase I (Topo I) and stabilize the DNA-Topo-I complex, ultimately resulting in the cell death. The rationale for the use of Topotecan in chronic lymphocytic leukemia (CLL) is based on the finding of Top-I being elevated in the lymphocytes of patients with this disease (O'Brien, S., Kantajian, H., Ellis, A., Zweling, L., Estey, E., Keating, M., Cancer, 75 (5) 104-1995).

Camptothecin and congeners represent a clinically very useful class of anticancer agents. The discovery that the (S) enantiomer of camptothecin (CPT), a compound isolated from the bark, leaves and fruit of *Camptotheca acuminata*, can kill cell through selective poisoning of the human enzyme topoisomerase-I bound to its substrate DNA, was important breakthrough for its development as an anticancer agent, The intact 20-(S)-lactone form of CPT first isolated over 30 years ago, (Wall, M. E., Wani, M. C., Cooke, C. E., Palmer, K. H., McPhail, A. T., J. Am. Chem. Soc. 88 3888 1966) can bind non-covalently to the complex formed by topoisomerase-I and DNA thus inhibiting the resealing of broken DNA backbone. The intrinsic ability of CPT to trap this complex has been clearly linked to antitumor activity especially for tumors over-expressing topoisomerase-I such as colorectal and cervical cancer (Tahimoto, C. H., Wright, H. J., Arbuck, S. G., Biochim. Biophys. Acta 1400 107 1998 and Iyer, L., Ratain, M. J., Cancer Chemotherapy Pharamcol 42 31 1998). Nanomolar concentrations of the drug are in fact sufficient to cause DNA damage in vivo, which becomes irreversible following its collision with DNA processing machineries. This collision event produces irreparable damage to the DNA (Hsiang, Y. H., Lihou, M. G., Liu, L. F., Cancer Res. 49 5077 1989) and finally results in cell death (Tsao, Y. P., Arpa, D., Liu, L. F., Cancer Res. 52 1823 1992 and Holm, C., Covey, J. M., Kerrigan, D., Pommier, Y., Cancer Res. 49 6365 1989). CPT is not an optimal drug as it exhibits very limited water solubility in addition to severe toxicity and erratic absorption. Despite its serious side effect, it has become such a promising antitumor agent that extensive research, considering both pharmokinetics and pharmacodynamic has led to the successful development of new closely related compounds. 10-Hydroxy-(20S) camptothecin (HCPT) was shown to possess therapeutic effect on liver carcinoma, leukemia, cancers associated with head and neck. 10-Hydroxy-(20S)-camptothecin was reported to show improved antitumor activity and was found to be ten times more potent against P-388 and 1210 mouse leukemia than the parent camptothecin and was found also to be less toxic. The hydrophobicity of CPT precluded its development as a clinical agent and necessitated the use of the hydrophilic synthetic congeners in various phases of clinical trails, 10-Hydroxycamptothecin has been isolated as a minor compound (0.002%) from the extra of stem wood of *C. acuminata* by Wall, M. E., & Wani, M. C., (J. Org. Chem. 34.1364 1969) and *Ophirrhiza mungos* Linn Tafur, S., Nelson, J. D., Delong, D. C. and Svobodo, G. H., Lloydia 39 261 1976). Wani, M. C., (J. Med. Chem. 23(5) 554 1980) reported the total synthesis of (dl)-9-[(dimethylamino)-methyl]-10-hydroxycamptothecin with the ring E intact involving a number of steps. However, the method gives a low yield and therefore is only of academic value.

Kingbury, W. D., (J. Med. Chem. 31 98 1991) converted CPT to HCPT by reduction-oxidation sequence using platinum catalyst to afford mixture of compounds including 10-acetoxycamptothecin and unreacted CPT. This method of preparation is not economically viable. Among HCPT congeners Camptosar (Irinotecan HCl CPT-11 by Pharmacia & Upjohn) and Hycamtin (Topotecan HCl TPT SmithKline Beecham Pharmaceutical) have been approved for the treatment of metastatic colorectal carcinoma and small cell lung cancer along with refractory ovarian cancer.

New potent and water soluble derivatives have been synthesized and are now in clinical studies while other potent drugs are in pre-clinical stage as second generation camptothecin. Functionalization at 7,9,10, positions is compatible with increase in activity as shown by the 9-amino-20-(S)-camptothecin, Lurtotecan (G-I147211) (Takimoto, C. H., Wright, J. S., Arbuck, G., Chemother. Pharmacol. 42 1400 1998) and Exetecan (Dx-8951) (Mitsui, I., Kumazawa, E., Hirota, Y., Aonuma, M., Sugumori, M., Ohsuki, S., Uoto, K., Ejima, A., Tersawa, H., Sato, K., Jpn, J Cancer Res. 88 760 1995).

OBJECTS OF THE INVENTION

The main object of the present invention is to present an improved process for the preparation of Topotecan-HCl from 10-Hydroxycamptothecin by aminoalkylation, using dihalomethane, viz. dichloromethane, dibromomethane, or diidomethane as a reagent, by unconventional Mannich reaction.

Another object of the invention is to obtain better yield than by classical methods of inducting C-1 unit using low boiling, low density and less toxic reagent, dichloromethane in place of formaldehyde.

Another object of the invention is to carry out reaction under mild conditions at low pressure and at room temperature with high reactivity and to prevent at the same time polyalkylation, which is a problem for electron-rich phenolic substrate.

Another object is to obtain Eschenmoser's salts (N-methyl-N-methylenmethaniminium salts) which follow the reaction pathway in which soluble and reactive "ion pair" formed after gegenion exchange from potassium ortho phenolate and Escheumoser's salts which eventually collapses to give ortho-attacked products.

Another object of the invention is to compare the behavior of protic/aprotic solvents for ortho-regiospecific monoalkylated products.

SUMMARY OF THE INVENTION

Accordingly the present invention provides a process for preparing 9-[(dimethylamino)-methyl]-10-hydroxycamptothecin(topotecan) of the formula I below

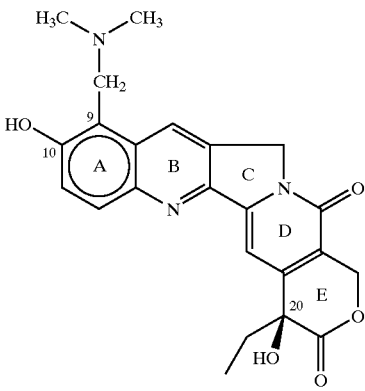

Topotecan(TPT)

from 10-hydroxy-20-(S)-camptothecin (HCPF) dissolved in an organic solvent, the process comprising ortho-regioselective aminomethylation of HCPT with dimethylamine, using a dihalomethane which behaves both as solvent and a reactant, under solid-liquid phase transfer catalysis along with a solid base catalyst in suspension form, and under stirring and at room temperature, filtering the solid product obtained and washing the obtained solid product, evaporating the solvent and purifying the residue to obtain the desired product.

In one embodiment of the invention, the dihalomethane is selected from he group consisting of dichloromethane, dibromomethane and diiodomethane.

In another embodiment of the invention, the solvent medium is selected from the group consisting of methylene halides, toluene, acetonitrile, dimethylformamide and any mixture thereof.

In yet another embodiment of the invention, the solid base catalyst is selected from the group consisting of potassium carbonate, sodium carbonate, ammonium carbonate, lithium carbonate and hydrated potassium carbonate.

In a further embodiment of the invention, the stirring is done at a pressure in the range of 10–18 psi. for a period of 4–8 hours.

In a further embodiment of the invention, the reaction is carried out at a temperature in the range of 25° C.–45° C. and on a rotary shaker at 220–250 rpm.

In another embodiment of the invention, the product topotecan obtained is in the form of a acetate or a hydrochloride salt by freeze drying.

In a further embodiment of the invention, the acetate of topotecan is converted to the pure hydrochloride salt thereof by adding dilute aqueous hydrochloric acid to the solution of acetate salt of topotecan followed by lyophilization.

In another embodiment of the invention, filtered residue is washed with ethyl acetate.

The obtained residue is preferably purified by repeated recrystallization or by distillation.

DETAILED DESCRIPTION OF THE INVENTION

Purification of the product may be effected by conventional chromatography or by repeated crystallization and finally characterized by physico-chemical techniques.

10-Hydroxycamptothecin up to 99% purity was stirred with anhydrous potassium carbonate along with dimethyamine and dihalomethane at room temperature 25° C. for 5 hours. The reaction was monitored by chromatographic techniques TLC, HPLC using different solvent systems at different wavelengths. The formation of the products was also determining by UV scanning, The substrate shows bathochromic shift when treated with dilute base. On TLC substrate (HCPT) shows orange colored spots, where as TLC chromatogram of the products shows yellow spot on UV (254 nm) on UV visualization. It is observed that toluene is solvent of choice for electron-rich phenols since it deceases polyalicylation whereas dichloromethane usually gives higher reactivity for substrate bearing electro-withdrawing groups.

The following examples are illustrative and not limiting of the scope of the invention. This description will clearly enable one skilled in the art to me and use the invention and describes several embodiments, adaptations, variations, alternatives and uses of the invention including what we presently believe is the best mode of carrying out the invention.

EXAMPLE I

A) 10-Hydroxycamptothecin was prepared by subjecting camptothecin (3.2 g 0.0092 mol), 0.8 g of $Pt^0$ (prepared by pre-reduction of 8 g of amorphous $PtO_2$ in 80 ml of HOAc for 1.5 hr under 1 atmosphere hydrogen pressure) and acetic acid to 1 atm. of $H_2$ for 8.5 h after which theoretical amount of $H_2$ absorbed (slightly more than 0.4 l) and uptake of $H_2$ gets slowed down The reaction mixture was degassed under steam of Helium and filtered through celite and washed with HOAc (20 ml). The resulting solution of 1, 2, 6, 7 tetrahydroxy-camptothecin was treated immediately with Pb (OAc)$_4$ (6.4 g 0.014 mol) in portions and reaction mixture, stirred vigorously under Helium for 30 min. Gumy residue was obtained on evaporation of solvent which was triturated with cold water (100 ml) to produce light brown solid. The solid was collected, washed with cold water and air dried overnight when a mixture of 10-HCPT (44%), 10-AcHOCPT (26%) and unreacted CPT (32%) on HPLC basis was obtained. This crude mixture was combined with 150 ml of 50% HOAc and heated under reflux conditions overnight The reaction mixture was cooled, concentrated to 20 ml and treated with cold water (100 ml) to produce precipitate, which is filtered, washed with more cold water and dried to afford 2.1 g of solid containing HCPT (70%) AcCPT (1.2%) and CPT (21.3%) on the basis HPLC. Mixture was triturating with 0.5% aq HCl to dissolve the water-soluble. When insoluble CPT was removed by filtration. Water-soluble was extracted with chloroform and crystallized from boiling solution of 20% of MeOH in CHCl$_3$ by adding EtOAC dropwise until turbidity appeared to obtain pure yellow HCPT which gives orange colored spot on TLC (CHCl$_3$, acetone, MeOH 7:2:1), C$_{20}$H$_{16}$N$_2$O$_5$ (m/s 364), mp 268–270° C. UV. λmax. 222, 266, 330 and 382 IR (KBr) 3480 (OH), 1740 (Lactone) and 1655 (pyridone) cm$^{-1}$; $^1$H NMR 0.88 (t, 3, C-18), 1.85 (m, 2, C-19 CH$_3$), 5.35 (s, 2, C-17), 6.40 (s, C-20 OH), 7.22 (s, 1H, C-14), 7.28 (m, C-11 and C-12), 7.26 (d, 1, C-9), 8.38 (1, s, C-7), 10.3 (s, br, C-10 OH).

9-[(Dimethylamino)methyl]10-hydroxy(20s)-camptothecin(Topotecan)

HCPT (0.364 g 0.01 mmol) and 40% aqueous dimethylamine (12 ml) was added in dichloromethane (50 ml) in which anhydrous potassium carbonate (2.17 g, 15 mmol) has been suspended The reaction mixture was stirred at room temperature for 5 hour, then filtered and solid extracted with ethylacetate (20 ml). The solvent is evaporated in vacuo giving a residue. The residue was triturated with 0.5% aq HCl (50 ml) to dissolve the water-soluble adduct. Water-soluble were partitioned with petroleum ether (3×50 ml) and followed by ethylacetate (3×50 ml). The aqueous layer was lyophilized as an off white hydrochloride salt yield 0.236 g (65%), C$_{23}$H$_{23}$N$_3$O$_5$. (m/s. 421.44); IR (KBr) 3400, 2960, 1740, 1650, 1590 cm$^{-1}$; $^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE II

HCPT (0.364 g 0.01 mmol) and 40% aqueous dimethylamine (12 ml) was added in dibromomethane (50 ml) in which anhydrous potassium carbonate (2.17 g 15 mmol) has been suspended. The reaction mixture was stirred at room temperature for 5 hour, then filtered and solid extracted wit ethylacetate (20 ml). The solvent is evaporated in vacuo giving a residue. The residue was triturated with 0.5% aq HCl (50 ml) to dissolve the water-soluble adduct. Water-soluble were partitioned with petroleum ether (3×50 ml) and followed by ethylacetate (3×50 ml). The aqueous layer was lyophilized as an off white hydrochloride salt yield 0.244 g (67%), C$_{23}$H$_{23}$N$_3$O$_5$. (m/s. 421.44); IR (KBr) 3400, 2960, 1740, 1650, 1590 cm$^{-1}$; $^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE III

HCPT (0.364 g 0.01 mmol) and 40% aqueous dimethylamine (12 ml) was added in dibromomethane (50 ml) in which anhydrous potassium carbonate (2.17 g 15 mmol) has been suspended. The reaction mixture was stirred at room temperature for 5 hour, then filtered and solid extracted wit ethylacetate (20 ml). The solvent is evaporated in vacuo giving a residue. The residue was triturated with 0.5% aq HCl (50 ml) to dissolve the water-soluble adduct. Water-soluble were partitioned with petroleum ether (3×50 ml) and followed by ethylacetate (3×50 ml). The aqueous layer was lyophilized as an off white hydrochloride salt yield 0.250 g (69%), C$_{23}$H$_{23}$N$_3$O$_5$. (m/s. 421.44); IR (KBr) 3400, 2960, 1740, 1650, 1590 cm$^{-1}$; $^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE IV

HCPT (0.364 g 0.01 mol) and 40% aqueous dimethylamine (12 ml) was added in dichloromethane (50 ml) in which potassium carbonate sesquihydrated (2.48 g 15 mmol) has been suspended. The reaction mixture was stirred at room temperature for 5 hour, then filtered and solid extracted with ethylacetate (20 ml). The solvent is evaporated in vacuo giving a residue. The residue was triturated with 0.5% aq HCl (50 ml) to dissolve the water-soluble adduct. Water-soluble were partitioned with petroleum ether (3×50 ml) and then followed by ethylacetate (3×50 ml). The aqueous layer was lyophilized as an off white hydrochloride salt; yield 0.218 g (60%) C$_{23}$H$_{23}$N$_3$O$_5$. (m/s. 421.44); IR (KBr) 3400, 2960, 1740, 1650, 1590 cm$^{-1}$; $^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5,29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE V

HCPT (0.364 g 0.01 mol) and 40% aqueous dimethylamine (12 ml) was added in dichloromethane (50 ml) in which anhydrous sodium carbonate (1.44 g 15 mmol) has been suspended. The reaction mixture was stirred at room temperature for 5 hour, then filtered and solid extracted with ethylacetate (20 ml). The solvent is evaporated in vacuo giving a residue, The residue was triturated with 0.5% aq HCl (50 ml) to dissolve the water-soluble adduct. The water-soluble were partitioned with petroleum ether (3×50 ml) and then followed by ethylacetate (3×50 ml). The aqueous layer was lyophilized as an off white hydrochloride salt; yield 0.124 g (34%) C$_{23}$H$_{23}$N$_3$O$_5$. (m/s. 421.44); IR (KBr) 3400, 2960, 1740, 1650, 1590 cm$^{-1}$;

$^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE VI

HCPT (0.364 g 0.01 mol) and 40% aqueous dimethylamine (12 ml) was added in dichloromethane (50 ml) in which potassium carbonate (2.78 g 20 mmol) has been suspended. The reaction mixture was stirred at room temperature for 5 hour, then filtered and solid extracted with ethylacetate (20 ml). The solvent is evaporated in vacuo giving a residue. The residue was triturated with 0.5% aq HCl (50 ml) to dissolve the water-soluble adduct. The water-soluble were partitioned with petroleum ether (3×50 ml) and then followed by ethylacetate (3×50 ml). The aqueous layer was lyophilized as an off white hydrochloride salt; yield 0.196 g (54%) C$_{23}$H$_{23}$N$_3$O$_5$. (m/s. 421.44); IR (KBr) 3400, 2960, 1740, 1650, 1590 cm$^{-1}$;

$^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE VII

HCPT (0.364 g 0.01 mol) and 40% aqueous dimethylamine (12 ml) was added in dichloromethane (50 mil) in which lithium carbonate (1.11 g 15 mmol) has been suspended. The reaction mixture was stirred at room temperature for 5 hour, then filtered and solid extracted with ethylacetate (20 ml). The solvent is evaporated in vacuo giving a residue. The residue was triturated with 0.5% aq HCl (50 ml) to dissolve the water-soluble adduct. The water-soluble were partitioned with petroleum ether (3×50 ml) and then followed by ethylacetate (3×50 ml). The aqueous layer was lyophilized as an off white hydrochloride salt, yield 0.113 g (31%), $C_{23}H_{23}N_3O_5$. (m/s. 421.44); IR (KBr) 3400, 2960, 1740, 1650, 1590 cm$^{-1}$;

$^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE VIII

HCPT (0.364 g 0.01 mol) and 40% aqueous dimethylamine (12 ml) in toluene was added in dichloromethane (50 ml) in which potassium carbonate (2.17 g 15 mmol) has been suspended. The reaction mixture was ted at room temperature for 5 hour, then filtered and solid extracted with ethylacetate (20 ml). The solvent is evaporated in vacuo giving a residue. The residue was triturated wit 0.5% aq HCl (50 ml) to dissolve the water-soluble adduct. The water-soluble were partitioned with petroleum ether (3×50 ml) and then followed by ethylacetate (3×50 ml). The aqueous layer was lyophilized as an off white hydrochloride salt, yield 0.149 g (41%). $C_{23}H_{23}N_3O_5$. (m/s. 421.44); IR (KBr) 3400, 2960, 1740, 1650, 1590 cm$^{-1}$;

$^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

EXAMPLE IX

A solution of HCPT (0.364 g 0.01 mol) and 40% aqueous dimethylamine (12 ml) in dimethylformamide was added in dichloromethane (50 mi) in which potassium carbonate (2.17 g 15 mmol) has been suspended. The reaction mixture was stirred at room temperature for 5 hour, then filtered and solid extracted with ethylacetate (20 ml). The solvent is evaporated in vacuo giving a residue. The residue was triturated with 0.5% aq HCl (50 ml) to dissolve the water-soluble adduct The water-soluble were partitioned with petroleum ether (3×50 ml) and then followed by ethylacetate (3×50 ml). The aqueous layer was lyophilized as an off white hydrochloride salt; yield 0.51 g (14%). $C_{23}H_{23}N_3O_5$. (m/s. 421.44); IR (KBr) 3400, 2960, 1740, 1650, 1590 cm$^{-1}$;

$^1$H NMR (CDCl$_3$) 1.04 (t, 3, J=7 Hz, C-18), 1.96 (q, 2, J=7 Hz, C-19), 2.01 (s, 3, CH$_3$CO$_2$), 2.50 (s, 6, (CH$_3$)$_2$NH), 4.20 (s, 2, ArCH$_2$N), 5.28 (d, 1, J=19 Hz, C-17), 5.29 (s, 2, C-5), 5.50 (d, 1, J=10 Hz, C-17), 7.42 (d, J=9 Hz, C-11), 7.67 (s, 1, C-14), 8.05 (d, J=9 Hz, C-12), 8.51 (s, C-7).

cl The Main Advantages of the Present Invention Are
1. Out of three solid bases used for solid-liquid transfer catalysis for ortho-aminomethylation of 10-Hydroxycamptothecin, potassium carbonate appears to be best choice for making 9-(dimethylamino)methyl]-10-hydroxy-(20s)-camptothecin(Topotecan).
2. Higher reactivity is obtained under mild conditions and polyalkylation is minimized with electron rich substrates as effect of solvent and base shows that yield of the product decreases dramatically in the absence of a base. Herein crude product can be isolated by simple filtration.
3. Dihalomethane has double role to play when it can behave both as a solvent and a reactant for rapid reaction with dimethylamine to form Manich adducts at atmospheric pressure.
4. Mannich products of 10-Hydroxycamptothecin have been isolated in good yield with methylene halide as a C-1 unit source, instead of formaldehyde.
5. Methylene halide and secondary amine react rapidly at room temperature and atmospheric pressure in basic conditions to form aminals (methylene-bisamines) as intermediates. In return, to our best knowledge, none of Mannich products have been obtained at atmospheric pressure, even after extended reaction times.
6. Solid-liquid transfer phase catalysis is straight forward route to desired products since use of Preformed-iminium salts (Mannich reagents) generally does not provide solution for aminoalkylation of indole, quinoline and isoquine alkaoids.
7. Effect of solvent and base on modal reaction shows that yield of the products decreases dramatically in the absence of any base or in the presence of amine like tri-butylamine It was also observed that it is not necessary to work in anhydrous conditions using potassium carbonate as a base.
8. Methodology provides superior yields, faster reaction under milder conditions, less undesired products for preparation of complex molecules. Where conventional Mannich procedure relies on the generation of aminomethyl species through equilibria involving an amine and formaldehyde which are only suitable for aminomethylation of electron-rich aromatic species and has limited scope when extended to less reactive substrates which are inert to classical Mannich conditions.
9. Though the yields while using dibromo and diodo methylenes were slightly higher, but keeping in view, the cost and the ease with which reagents are used dichloromethylene appears to be the best.

We claim:

1. A process for preparing 9-[(dimethylamino)-methyl]-10-hydroxycamptothecin(topotecan) of the formula 1 below

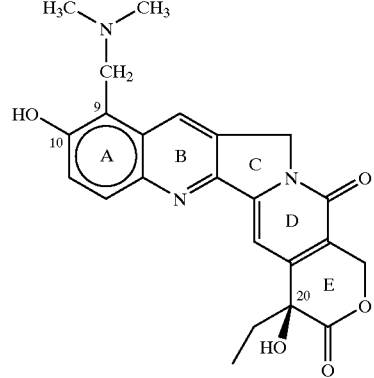

Formula I

Topotecan(TPT)

from 10-hydroxy-20-(S)-camptothecin (HCPT) dissolved in an organic solvent, the process comprising ortho-regioselective aminomethylation of HCPT with dimethylamine, using a dihalomethane which behaves both as solvent and a reactant, under solid-liquid phase transfer catalysis along with a solid base catalyst in suspension form, and under stirring and at room temperate, filtering the solid product obtained and washing the obtained solid product, evaporating the solvent and purifying the residue to obtain the desired product.

2. A process as claimed in claim 1 wherein the dihalomethane is selected from the group consisting of dichloromethane, dibromomethane and diidomethane.

3. A process as claimed in claim 1 wherein the solvent medium is selected from the group consisting of methylene halides, toluene, acetonitrile, dimethylformamide and any mixture thereof.

4. A process as claimed in claim 1 wherein the solid base catalyst is selected from the group consisting of potassium carbonate, sodium carbonate, ammonium carbonate, lithium carbonate and hydrated potassium carbonate.

5. A process as claimed in claim 1 wherein the stirring is done at a pressure in the range of 10–18 psi. for a period of 4–8 hours.

6. A process as claimed in claim 1 wherein the reaction is carried out at a temperature in the range of 25° C.–45° C. and on a rotary shaker at 220–250 rpm.

7. A process as claimed in claim 1 wherein the product topotecan obtained is in the form of a acetate or a hydrochloride salt by freeze drying.

8. A process as claimed in claim 1 wherein the acetate of topotecan is converted to the pure hydrochloride salt thereof by adding dilute aqueous hydrochloric acid to the solution of acetate salt of topotecan followed by lyophilization.

9. A process as claimed in claim 1 wherein the filtered residue is washed with ethyl acetate.

10. A process as claimed in claim 1 wherein the obtained residue is purified by repeated recrystallization or by distillation.

* * * * *